United States Patent [19]

Törnblom

[11] Patent Number: 4,864,235
[45] Date of Patent: Sep. 5, 1989

[54] PHASE-SELECTIVE MONITORING VIA VECTOR TRANSFORMATION

[75] Inventor: Bengt H. Törnblom, Västerås, Sweden

[73] Assignee: Tornbloms Kvaliteskontroll AB, Västerås, Sweden

[21] Appl. No.: 168,416

[22] Filed: Mar. 15, 1988

[30] Foreign Application Priority Data

Mar. 17, 1987 [SE] Sweden .............................. 8701082-3

[51] Int. Cl.$^4$ ...................... G01N 27/72; G01R 33/12
[52] U.S. Cl. ...................................... 324/233; 324/225
[58] Field of Search ................ 324/223, 233; 328/155; 307/511

[56] References Cited

U.S. PATENT DOCUMENTS

| 4,424,486 | 1/1984 | Denton et al. | 324/233 |
| 4,646,013 | 2/1987 | Tornblom | 324/225 |
| 4,661,777 | 4/1987 | Tornblom | 324/225 |

FOREIGN PATENT DOCUMENTS 351493 11/1972 Sweden .
7507857 1/1977 Sweden .
8400698 8/1985 Sweden .

Primary Examiner—Reinhard J. Eisenzopf
Assistant Examiner—Walter E. Snow
Attorney, Agent, or Firm—Watson, Cole, Grindle & Watson

[57] ABSTRACT

A defect-sensing device for a test object, e.g. for detecting cracks in metal bodies with the aid of the eddy-current technique, has improved phase-selective properties by adding at least one product and/or quotient former to the signal processing equipment. The output signal from an ordinary phase-controlled rectifier can be substantially described via $\sin \alpha$ and/or $\cos \alpha$ functions in which indicates the phase position of the control signal in relation to the input signal. By multiplying $\sin \alpha$ by $\cos \alpha$ $\sin 2\alpha \cos 2\alpha$ functions are obtained which in turn can be multiplied to obtain the function $\sin 4\alpha$ corresponding to narrow sensitivity lobes in the transducer's impedance plane, thus permitting effective separation of the various types of vector signal resulting from detectable defects.

7 Claims, 8 Drawing Sheets

PHASE-SELECTIVE MONITORING VIA VECTOR TRANSFORMATION

TECHNICAL FIELD

The present invention relates to a device for testing and/or measuring, which will herein be referred to as "monitoring", test objects (as later defined but which can be hot steel billets) with respect to at least one quantity such as a surface crack, which device comprises at least one phase-sensitive detector, (e.g. a synchronous detector) to generate at least one vector signal in the presence of said parameter, and at least one signal-operating means (such as multiplicator) to act on the at least one vector signal or measured values deriving from said at least one phase-sensitive detector.

The invention can be considered as a radical improvement in phase-discriminating techniques when employing eddy current testing. One result is that the need to use several carrier frequencies is reduced in some cases, thanks to the improved phase discrimination obtainable by virtue of the invention. In some cases the invention offers the same possibilities and advantages as the use of additional frequencies.

DISCUSSION OF PRIOR ART

Conventional defect-detecting equipment and equipment such as described in U.S. Pat. Nos. 4,646,013 and 4,661,777 usually operate with a simple type of phase-controlled detector. These detectors show maximum sensitivity in one direction/phase, which is displayed 90° to the direction for minimum sensitivity.

Since, as described in U.S. Pat. No. 4,646,013, various types of vectors often have directions in the impedance plane of the detector which only differ 15° to 25° from each other, it is extremely difficult to effectively separate the vectors from each other using conventional detectors since such detectors are not sufficiently phase-selective. A consequence of this is that it is not reliably possible to distinguish between quality-affecting defects in a test object and surface blemishes which do not have any quality-affecting significance.

SUMMARY OF THE INVENTION

The present invention offers solutions to these and other associated problems and is characterised in that at least one of the vector signals obtained from the at least one detector device is supplied to the at least one signal-operating means and is there subjected to vector transformation in order to improve the separation between different types of vectors.

A particularly important vector transformation is product and/or quotient generation.

DEFINITIONS OF TERMS USED

To facilitate understanding of the following description, and the abbreviations and designations used, the following definitions should be noted:

TEST OBJECT should be taken to mean inter alia a wire, rod, billet, sheet or stream of a liquid medium, which may be at any temperature.

TRANSDUCER should be taken to mean a transducer, sensor or probe, and combination thereof.

QUANTITY should be taken to cover a test object defect, surface crack, shape, dimension, position, flux, velocity or stress.

Phase-sensitive DETECTOR should be taken to mean inter alia a phase-controlled, a phase-sensitive or a synchronous rectifier or detector.

LO means lift-off.

SPR means a crack.

GSK means a non-quality-affecting quantity such as oxide scale.

LOBE (L) means the curve representing the sensitivity of a device in different directions in at least one two-dimensional plane, e.g. the impedance plane of an eddy-current transducer. (The similarity to the directional action of a radio antenna may be mentioned by way of comparison).

$|A|$ means the magnitude or value of a vector A.

$\alpha$ will be used for the angle or phase difference between the control signal and input signal of a detector.

$\beta$ will be used for the angle or phase difference between two vectors.

$(\phi+0°)$ and $(\phi+90°)$ means that the phase difference between these signals is 90°, and that the signals have a phase difference $\phi$, which may be varied in relation to another signal, e.g. $A \sin \omega t$. In other words, the signals $(\phi+0°)$ and $(\phi+90°)$ have a fixed phase position in relation to each other. At the same time these signals have phase positions which differ $(\phi+0°)$ and $(\phi+90°)$, respectively, from the phase position of e.g. $A \sin \omega t$.

DIRECTIONAL DERIVATIVE $(dL/d\phi)$ means the derivative of sensitivity as a function of direction. It can also be expressed as the sensitivity variation per change of direction.

FREQUENCY or CARRIER FREQUENCY will be taken to mean the frequency or frequencies with which a transducer is supplied, e.g. $\omega_L$ and $\omega_H$. Frequency also includes a frequency component.

VECTOR TRANSFORMATION means, inter alia technology such as revealed in FIG. 7. This is taken from an article by Hugo L. Libby. Other examples of vector transformation are given in Swedish patent specifications 7507857-6, 8400698-0 and application Ser. No. 146,175, filed Jan. 20, 1988.

Thus in this description, the phrase vector transformation means all variants and imaginable combinations of the above-mentioned principles and embodiments.

BRIEF DESCRIPTION OF THE DRAWINGS

The invention will now be further described, by way of example, with reference to the accompanying drawings, in which.

The embodiments of the invention described in the following with reference to the drawings should be considered as one of many feasible examples and embodiments. Many other applications are also possible. The Figures are not drawn to scale and should therefore only be considered as diagrammatic sketches.

The invention aims to provide a detecting device having improved phase-discrimination properties. As can be seen from U.S. Pat. No. 4,646,013, the angle between the LO-vector and an error vector, e.g. $F_L$, is in the order of 15° to 25° at normal frequencies. Particularly at slightly higher frequencies the GSK vectors tend to approach both SPR and LO vectors. Consequently it is difficult, in some cases impossible, to separate the vectors from each other using conventional phase-discrimination techniques based on the use of simple phase-sensitive detectors. The sensitivity lobes of these conventional devices correspond to, for example, the sin $\alpha$ and cos $\alpha$ curves shown in FIG. 3.

DESCRIPTION OF PREFERRED EMBODIMENTS

Figure 1:
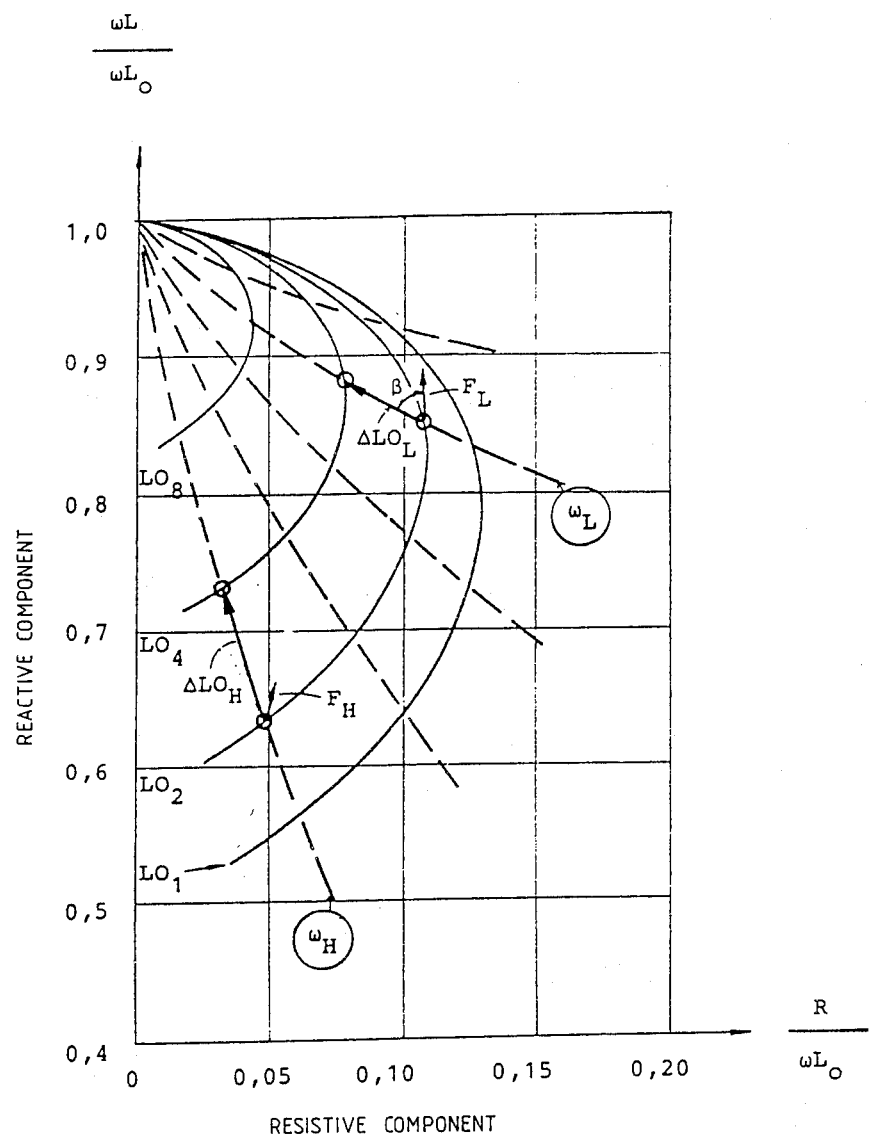
FIG. 1 shows an impedance diagram.

FIG. 1 shows a familiar impedance diagram for a surface transducer coil supplied by eddy currents. FIG. 1 is described in detail in U.S. Pat. No. 4,646,013 from which the figure is taken and plots the reactive component as ordinate and the resistive component as abscissa. The curves $LO_1$ to $LO_8$ represent different LO distances and the curves $\omega_L$ and $\omega_H$ represent different carrier frequencies. It should be noted that the $\alpha$ used in FIG. 1 of U.S. Pat. No. 4,646,013 has been altered to $\beta$ in the FIG. 1 attached to avoid confusion with the other designations used later.

Figure 2:
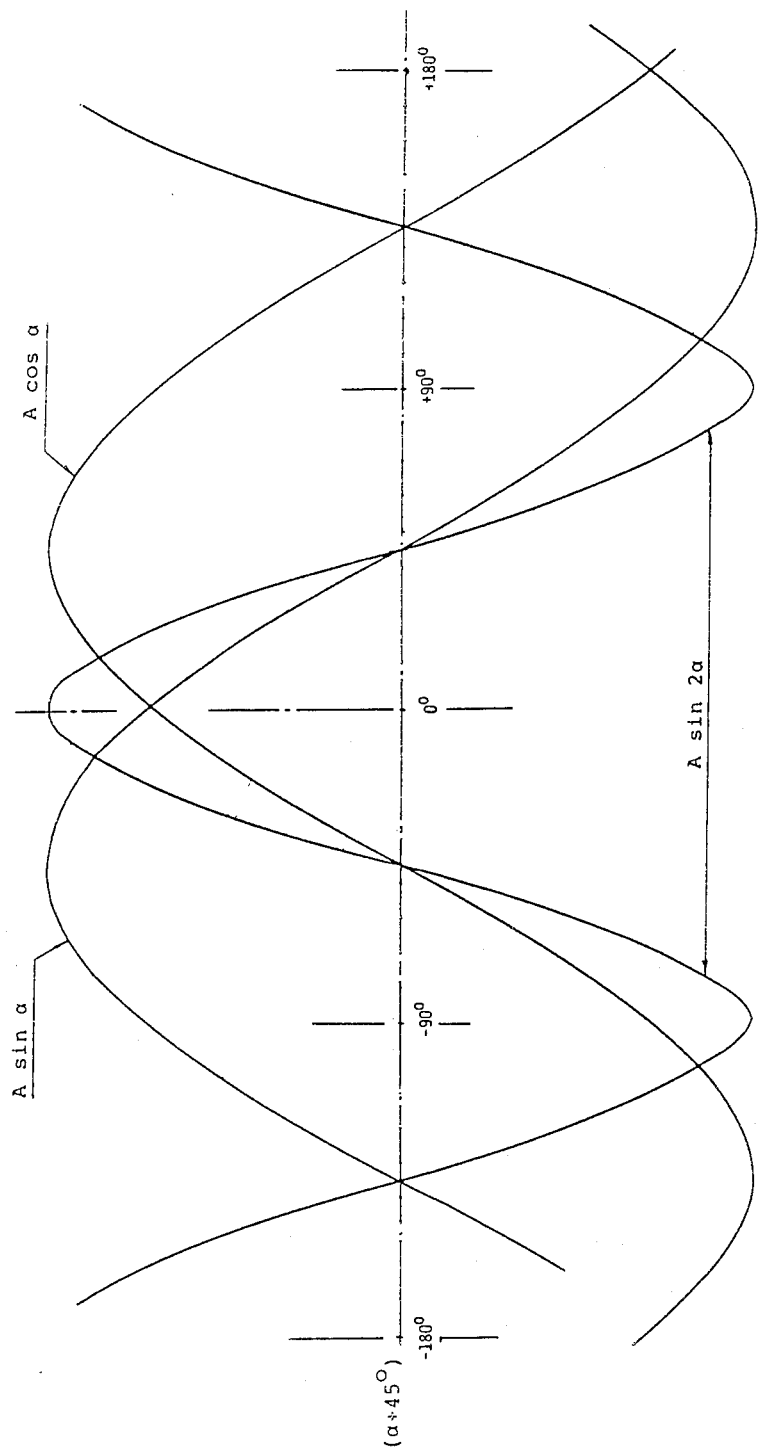
FIG. 2 the output function from phase-controlled detectors.

FIG. 2 shows graphically the output functions A sin $\alpha$ and A cos $\alpha$ from phase-controlled detectors where the control phases are displaced 90° in relation to each other, and a function A sin $2\alpha$ obtained by forming a product. The functions sin $\alpha$ and cos $\alpha$, respectively, show the output signal as a function of phase position of the control signal in relation to the input signal. The angle $\alpha$ may be considered here as the phase position of the detector's control signal in relation to the phase position of the detector's input signal (A sin $\omega t$). The angle $\alpha$ corresponds to a certain direction of the vector in the impedance plane shown in FIG. 1.

Whether a signal is to be considered as a sine or a cosine signal is dependent on which phase angle is used as the reference position/phase.

Figure 3:
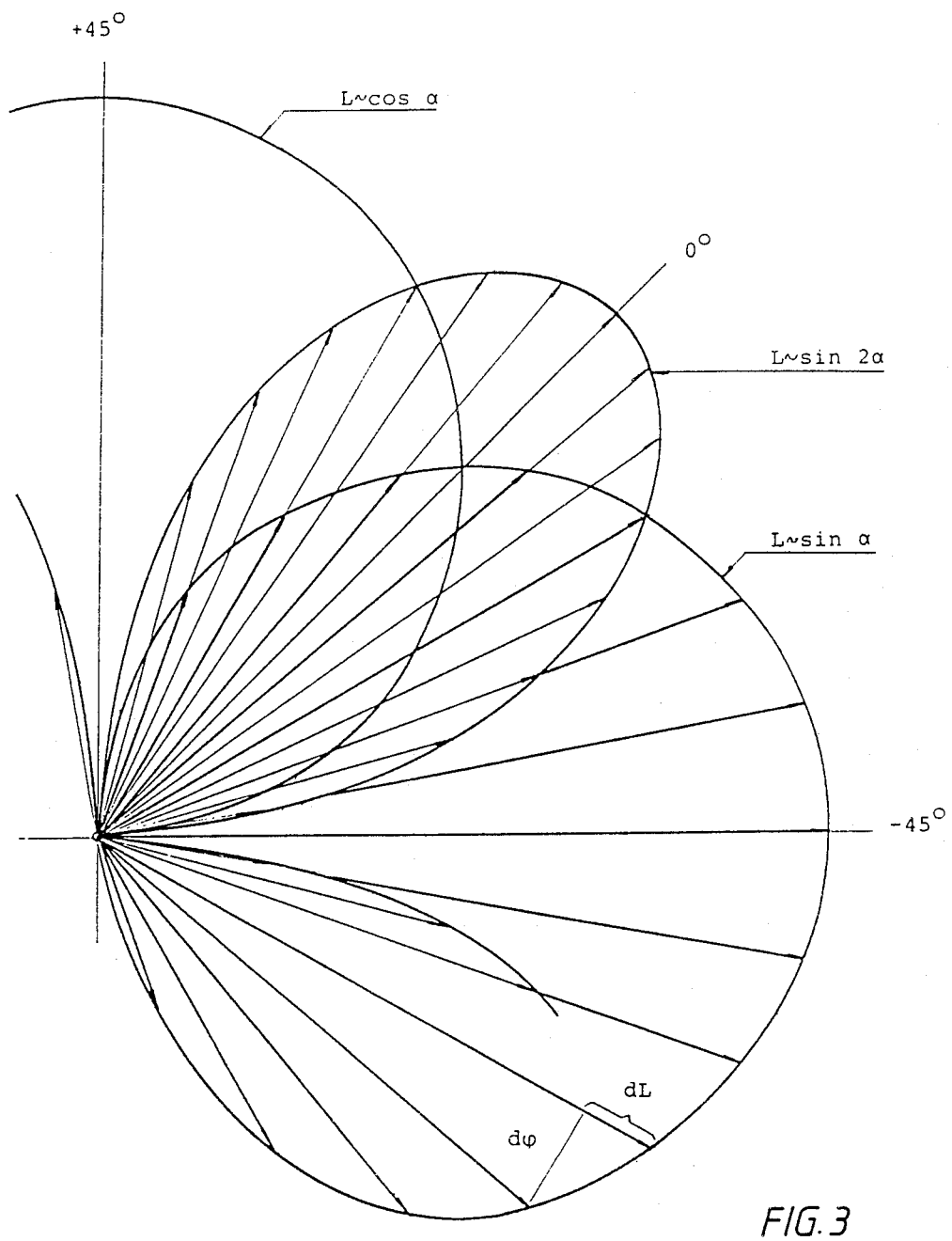
FIGS. 3 and 4 sensitivity lobes.

FIG. 3 shows sensitivity lobes or simpler lobes (L) pertaining to the functions in FIG. 2.

Since correspondence to $\alpha$ exists in FIG. 1, these lobes can be placed in FIG. 1. The vectors in FIG. 1 can then be detected by the device or a part thereof, with a sensitivity which is, to at least a certain extent, determined by the extension of the lobe in the relevant direction. The lobes L in FIG. 3 are proportional to the functions sin $\alpha$, cos $\alpha$ and sin $2\alpha$.

Figure 4:
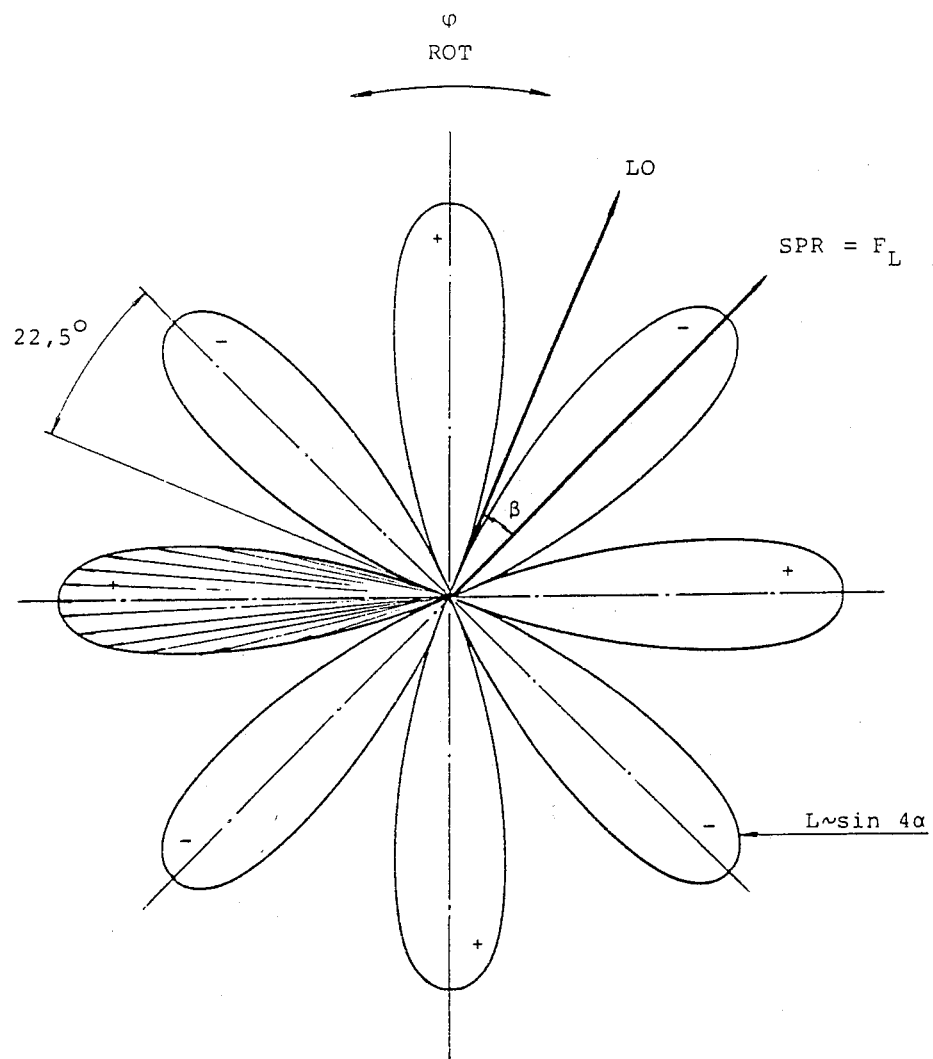

FIG. 4 shows lobes corresponding to the function sin $4\alpha$, i.e. they are narrower or, put another way, more selective. FIG. 4 also shows that the lobes can be turned or rotated (ROT) in relation to the vectors LO and SPR. The lobes are alternately positive and negative.

Figure 5A:
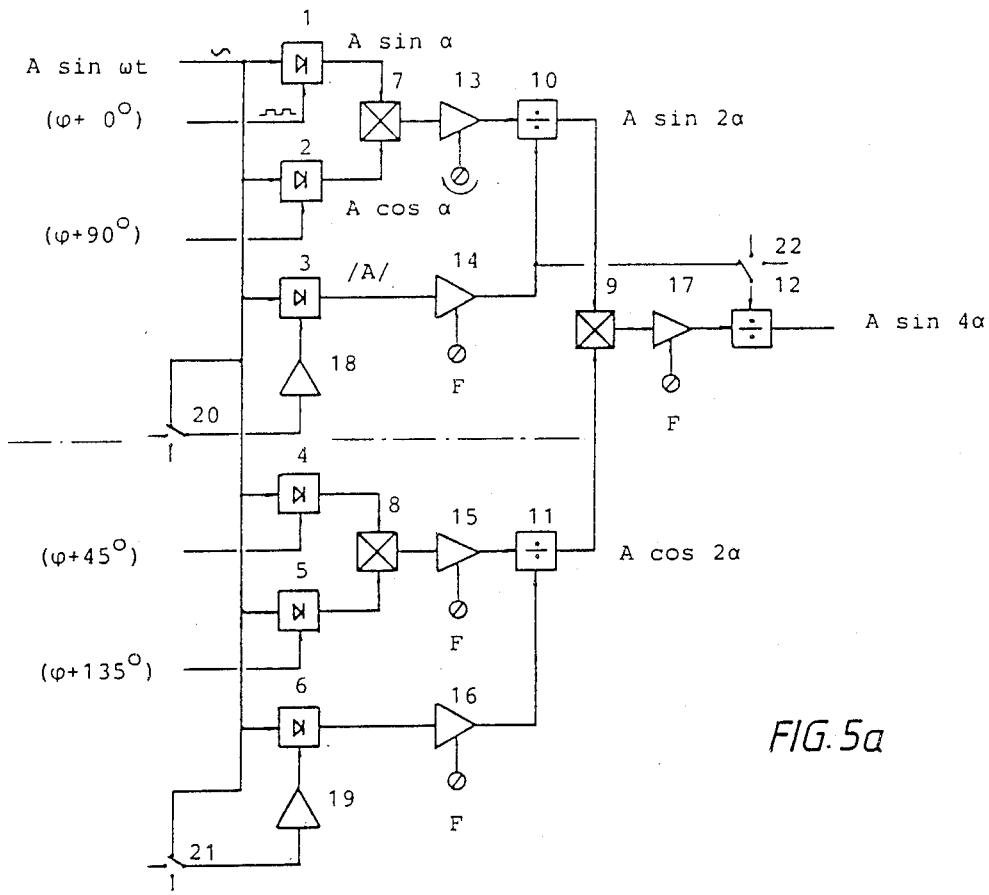
FIGS. 5a, 5b and 6 show circuit diagrams of embodiments of devices according to the invention.
Figure 5B:
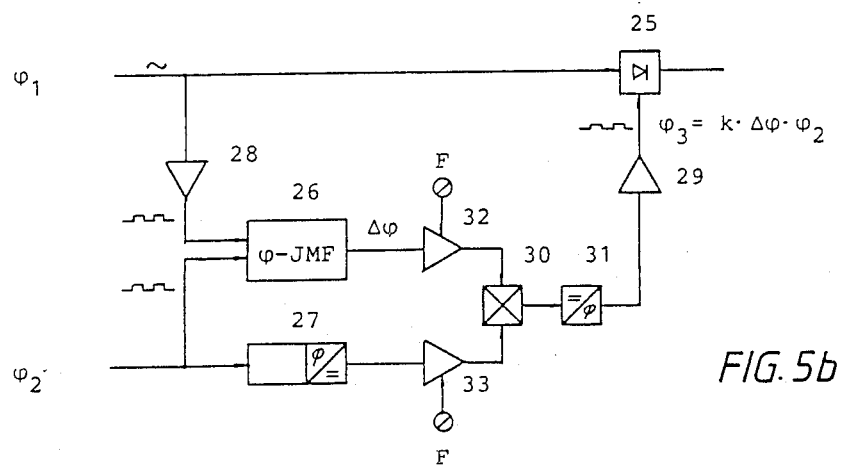

FIGS. 5a and 5b show in block circuit format two different embodiments of devices according to the invention, where the phase-discrimination technique is further developed via product and quotient formation.

Figure 6:
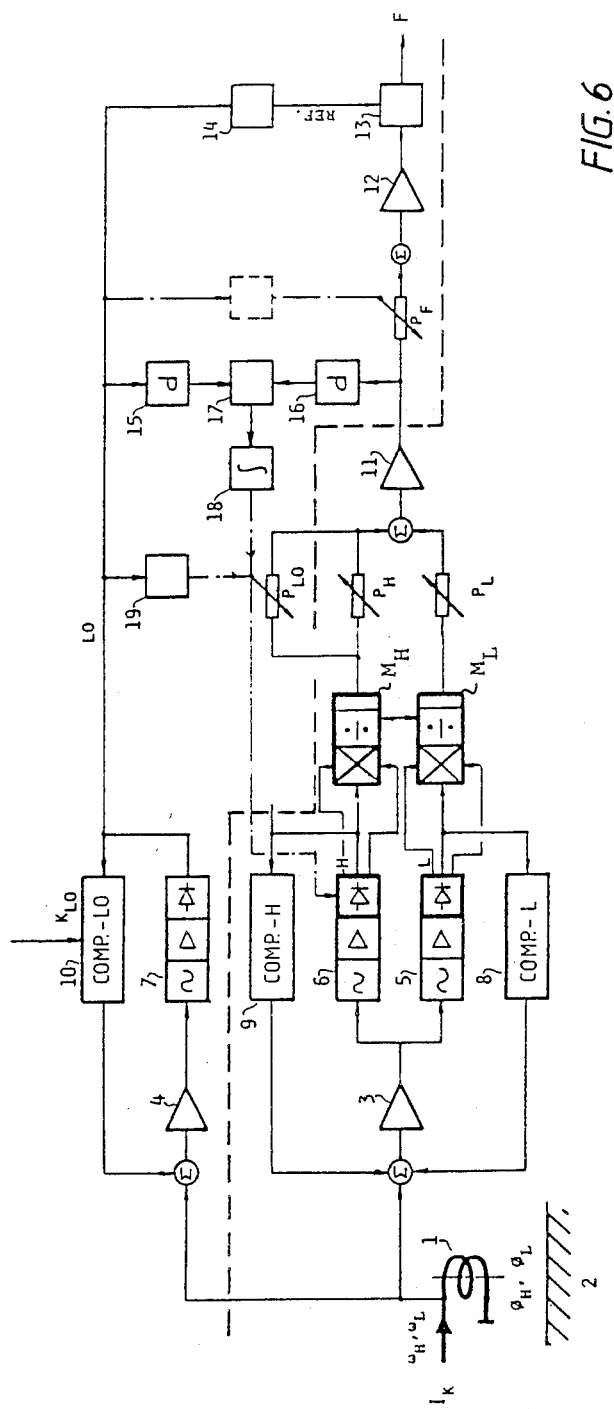

FIG. 6 shows one of many examples of how a device according to the invention may be constructed. FIG. 6 is taken from U.S. Pat. No. 4,661,777 where it is included as FIG. 3. The item numbers therefore refer to the description in that prior published U.S. patent specification. To FIG. 6 have been added blocks according to FIG. 5a, these being indicated by heavier lines in FIG. 6 and designated $M_H$ and $M_L$, respectively, thus revealing the characteristic features of the present invention.

Figure 7:
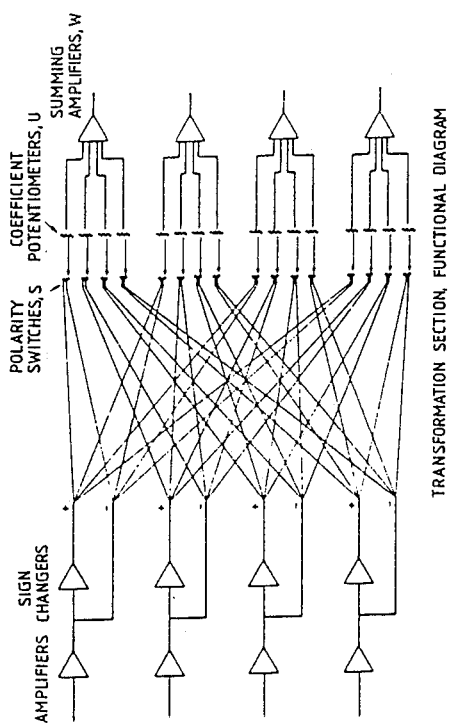
FIG. 7 shows one form of vector transformation.

Note, however, that here there are two blocks, each of which corresponds to FIG. 5a, with input signals of different frequencies, i.e. $A_1$ sin $\omega_H t$ and $A_2$ sin $\omega_L t$, respectively. The number of detector/rectifiers in FIG. 6 has, for instance, been increased to three per channel. The output signals from these supply the product and quotient blocks, $M_H$ and $M_L$. The blocks $M_H$ and $M_L$ then supply the subsequent transformation circuits, which may also be designated as shown in FIG. 7. Note also the cross-connection between $M_H$ and $M_L$, showing that transformations (e.g. products) can be formed having different carrier-frequency origin.

FIG. 7 shows a simplified diagram of how a signal operating means to create a vector transformation can be arranged. The input signals here consisted previously of sin $\alpha$ and cos $\alpha$—terms from simple phase-controlled rectifiers. According to the present invention, these functions are supplemented or replaced by sin n.$\alpha$ and/or cos n.$\alpha$, terms in which n can be any number.

By way of example, the input signals may refer to sin $\alpha$, sin $2\alpha$, sin $4\alpha$, cos $\alpha$, cos $2\alpha$ and cos $4\alpha$, etc. As will be appreciated, the variations are almost unlimited.

Both in the known technology and in the new technology according to the present invention, the sine and cosine terms may derive from different carrier frequencies or combinations thereof.

Combined with vector transformation and dynamic transformation as defined in U.S. Pat. No. 4,661,777, the invention offers unique possibilities and properties included in the present invention in their more sophisticated form.

If two simple phase-sensitive detectors, for example those marked 1 and 2 in FIG. 5a, are supplied with control signals ($\phi + 0°$) and ($\phi + 90°$), respectively, it is known that the following functions A.sin $\alpha$ and A.cos $\alpha$, respectively can be obtained. These functions are plotted graphically in FIG. 2. It should be mentioned that the angle need not be 90° and was selected primarily because it is easier to work with. From the simple trigonometric formula $$\sin 2\alpha = 2.\sin \alpha.\cos \alpha \qquad \text{Equation 1}$$

it is seen that, multiplication of the sine and cosine terms gives the function sin $2\alpha$. The function sin $2\alpha$ is also plotted in FIG. 2. It is readily apparent that the signal A sin $2\alpha$ is considerably more phase-selective than sin $\alpha$, because of its larger derivative for phase-alterations than the signal A sin $\omega t$. This is shown in FIG. 3 where the lobes for sin $\alpha$ and cos $\alpha$, respectively, are compared with the narrower lobe for sin $2\alpha$, which is always more phase-selective. In other words, with the aid of a multiplicator 7 in FIG. 5a, a better, more directionally selective, sensitivity function has been obtained.

Since the input signal to the detectors 1 and 2 in FIG. 5a derives from a magnitude, it can be written as A sin $\omega t$ where $|A|$ constitutes the magnitude. This means that it may be advisable to also take into consideration the influence of the amount on product formation since, of course, $$A \cdot \sin \alpha \cdot A \cdot \cos \alpha = \frac{A^2}{2} \sin 2\alpha. \qquad \text{Equation 2}$$

Items 3 and 5 in FIG. 5a are therefore connected as amplitude-sensing detectors, and are thus not dependent on direction, since comparators 18 and 19 have inputs connected via switches 20, 21 to the input signals of the detectors, i.e. to the signal A. sin $\omega t$. The output signal from detector 3 thus corresponds to magnitude $|A|$ of A. By dividing $A^2/2$ sin $2\alpha$ by $|A|$ in a quotient former 10, a function A sin $2\alpha$ is obtained, as can be seen in FIG. 5a. If $A^2$ had been retained instead of A as now, an exponential response would have been obtained which is not always so simple to deal with. Quotient forming thus allows the magnitude of the sensed quantity to be retained in spite of product formation.

It can also be seen from FIG. 5a that the detectors 1, 2 and 3, the multiplicator 7 and the quotient former 10 can be considered as a first channel, and the detectors 4, 5 and 6, a multiplicator 8 and a quotient former 11 as a second channel. The two channels are identical except that the control signals differ by 45° between the channels. Due to the product formation, this difference is doubled from 45° to 90°, whereby sine and cosine terms are obtained, namely A sin $2\alpha$ and A cos $2\alpha$, respectively. Units 13, 14, 17, 18, 15, 16 and 19 in FIG. 5a are amplifiers.

The functions A sin $2\alpha$ and A cos $2\alpha$ can then be multiplied in a product former/multiplicator 9, the function A sin $4\alpha$ then being obtained after a second quotient formation at 12. The function A sin $4\alpha$ is shown in lobe form in FIG. 4. The angle between max and min sensitivity is here 22.5°, which is extremely advantageous since this angle corresponds to the angle between the LO vector and the SPR vector.

Thus the LO vector can be efficiently suppressed and the SPR vector detected with high reliability.

To get the LO vector to fall between two adjacent lobes, the lobe picture can be turned in relation to the vectors. This turning movement or rotation (ROT) can easily be obtained by varying $\phi$ in FIG. 5a. If desired, turning can be performed automatically while e.g. the LO vector is studied. The rotation can be automatically stopped when the LO vector becomes a minimum, which means that the LO suppression is optimized.

It should be noted that it is primarily a suppression of the LO vector that is sought and that it is sufficient if the SPR vector falls within a part of a lobe which has relatively high sensitivity. The SPR vector need not necessarily fall exactly on the normal mid-line of the lobe.

If desired, the function A. sin $4\alpha$ may be used to generate a further function A sin $8\alpha$ or even higher multiples should further phase-separation be required.

Similarly, the control signals fed to the two channels in FIG. 5a may be allowed to differ by an angle other than 45°, thus generating more irregular lobes and lobe patterns. The possibilities are thus almost unlimited.

One consequence of the narrow lobes, enabling separation of vectors differing by a small angle ($\beta$) is a dramatic improvement in the criteria for effective vector transformation. Several frequencies, e.g. $\omega_L$ and $\omega_H$, can then be used and, if advantageous, products can be formed from signals having different carrier-frequency origin.

It is also possible to combine certain lobes, for instance, and to block others, so that, for example, only the lobes in one quadrant are active. The same effect can be achieved by making use of the polarity of each lobe. The lobes or "petals" not desired in the "flower" in FIG. 4 can thus be removed, retaining only those, for instance, which are of value to a required vector separation.

The invention can also be used to combine or supplement the simulated transducer and transducer movement described in our recently filed U.S. patent application claiming priority from U.S. patent application Ser. No. 152,545, filed Feb. 5, 1988.

In its purest form, the invention may be considered to be characterized in that lobes are generated as functions of product and/or quotient forming. The lobes, as well as the product formers/multiplicators, may be direct or indirect type. By "indirect type" is a meant that product or quotient forming occurs with different circuits, i.e. a kind of detour where the function can be equated with a multiplicator in some form. Both product and quotient forming may include non-linear functions and equations.

In conclusion, FIG. 5a should be considered as one example of how the invention, somewhat simplified, can be realized starting with simple trigonometric equations, often offering symmetrical lobes which are easy to adapt to relevant vectors and vector types. The signal A sin $\omega t$ in FIG. 5a may be the same or similar to the signals from item 3 in FIG. 3 of U.S. Pat. No. 4,661,777. Items 5 and 6 in the same Figure are preferably replaced by circuits according to FIG. 5a in this application.

FIG. 5b illustrates a slightly different detector device. The intput signal to a detector 25 is here designated $\phi_1$, which should be considered as a phase value. A reference phase is designated $\phi_2$ and the control signal/phase to the detector 25 is designated $\phi_3$.

A comparator 28 converts the input signal $\phi_1$ to a square signal which is compared with $\phi_2$ in a phase-angle comparator 26. The output signal from 26 thus gives the phase difference between $\phi_1$ and $\phi_2$, in other words $\Delta\phi = \phi_1 - \phi_2$. The signal $\Delta\phi$ is provided with a suitable coefficient in an amplifier 32 before being used as one of the input signals to a multiplicator 30. The signal $\phi_2$ is converted in a signal-operating means 27 to a direct voltage which is provided with a suitable coefficient in an amplifier 33, the output signal from this amplifier constituting the other input signal to the multiplicator 30. In a converter 31 the product signal from the multiplicator 30 is again converted to a phase signal which is amplified/pulse-formed in a comparator 29, the output signal from this comparator being $\phi_3$. $\phi_3$ is thus the result of a product formation and $\phi_3 = k.\Delta\phi.\phi_2$, where k is a selected constant. The control signal $\phi_3$ thus varies in phase in proportion to the product $k.\Delta\phi.\phi_2$. The result is that the output signal from the detector 25 will be much greater than the $\Delta\phi$-change in $\phi_1$ itself would have warranted.

Here, too, the result is that, due to the product formation, an amplified directional derivative ($dL/d\phi$) is obtained. However, an arrangement according to FIG. 5b will give a different lobe picture from the arrangement according to FIG. 5a. Both variants, however, have their advantages.

Obviously, in principle, any trigonometric formula containing a product or a quotient may be used within the scope of the invention and will in all likelihood give rise to a specific lobe picture and pattern which could be of commercial use.

The product formers may consist of a wide range of signal-processing equipment included amongst which may be mentioned hardware-based multiplicators, software-based computers, balanced modulators and log-antilog-amplifiers.

The following list shows the significance of the designations in FIGS. 5a and 5b.

| Item | Type |
|---|---|
| 1,2,4,5 | Phase-sensitive detector. |
| 3,6 | Phase-sensitive detector connected to |

| Item | Type |
| --- | --- |
|  | amount sensing detector. |
| 7,8,9 | Product former, e.g. multiplicator. |
| 10,11,12 | Quotient former. |
| 13,14,15,16,17 | Amplifier, variable gain. |
| 18,19 | Pulse former, e.g. comparator. |
| 20,21,22 | Converter, selection of denominator type. |
| 25 | Phase-sensitive detector. |
| 26 | Phase comparator. |
| 27 | Phase to DC converter. |
| 28,29 | Pulse former, e.g. comparator. |
| 30 | Product former, e.g. multiplicator. |
| 31 | DC to phase-convertor. |
| 32,33 | Amplifier, variable gain. |

From the foregoing description and the above list, the reader should have no difficulty in understanding the function of the invention in principle. However, it should be observed that hierarchical networks of a complex nature can be constructed using FIGS. 5a and 5b and their constituent parts.

All imaginable networks and combinations are of course covered by the invention. Similarly, such embodiments are also included where varying carrier frequencies are used. The varying frequency can then be seen as a different way of expressing the phase measurement/discrimination described in this invention, but comprises in principle the same information. Product formation and/or quotient formation based on frequency variation is thus included in the invention.

The product formation can be performed with either analog or digital signals or measured values, depending on which is considered most suitable.

It should again be emphasized that the lobes in FIGS. 3 and 4 can refer to the impedance diagram in FIG. 1. The center of the lobes is then suitably placed to coincide with the working point in the impedance plane. There is nothing to prevent the lobes from having different appearances at different frequencies. If the lobes derive from several frequencies, this must of course be taken into consideration.

To summarize, the invention may be seen as a method and/or means for monitoring test objects with respect to at least one quantity comprising the use of at least one transducer and including at least one detector to detect at least one signal derived at least partly from the at least one transducer, and at least one device to produce at least one of a product and a quotient of signals at least partially derived from the at least one transducer, and is characterized in that the directional derivative of at least one of the sensitivity lobes of the device, is at least partially made a function of the forming of the product and/or quotient so as to improve the effective phase discrimination of the device. Although the invention functions excellently at one carrier frequency, it is in combination with vector-transformation techniques that the invention offers vast improvements over conventional technology.

The following describes a variant within the scope of the invention.

If a vector such as $F_L$ in FIG. 1 is taken, and the quotient of its projections on the horizontal and vertical axes, respectively, is formed, this will give a measurement of the direction of the vector. Other projection axes can also be used as a reference if desired. Comparing the quotient value with predetermined quotient-value limits or functions will give an extremely phase-selective detection.

Figure 8A:
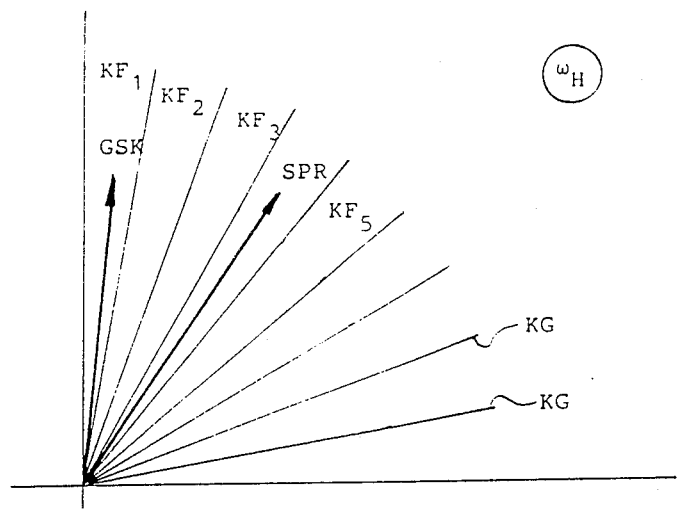
FIGS. 8a and 8b show details of FIG. 1.
Figure 8B:
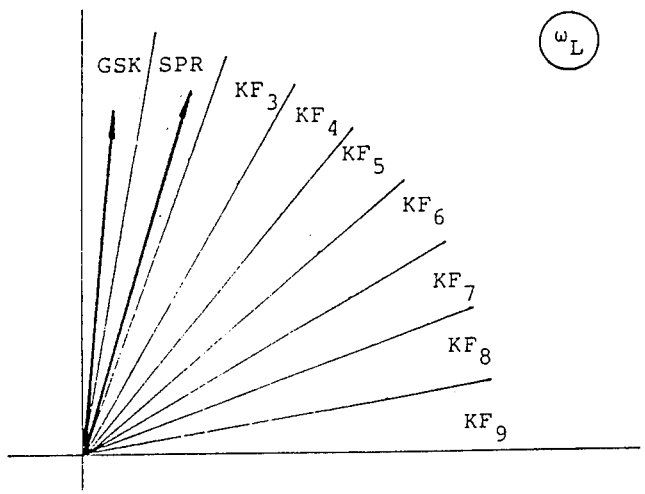

FIGS. 8a and 8b refers to FIG. 1 and shows the limits of the quotient fields $KF_1 \ldots KF_9$. Each quotient field can in reality consist of the quotient values of e.g. voltages within a voltage interval.

In FIGS. 8a and 8b different carrier frequencies are used, a high frequency $\omega_H$ being used in FIG. 8a and a lower frequency $\omega_L$ in FIG. 8b.

In FIGS. 8a and 8b it is seen that the SPR vector falls within different quotient fields for the two frequency cases being in field $KF_4$ in the high frequency case and in field $KF_2$ in the low frequency case. The criterion for GSK vectors can be set to fall in quotient fields $KF_1$ in both the high and low frequency cases.

If a graphic display is used, the quotient limits can be inserted on the screen.

As is evident, forming a quotient of the vector projections gives an extremely effective starting point for effective and selective monitoring of test objects.

If the quotient values in analog or digital form are included as input signals in condition circuits or condition functions, for instance, a simple device results which has sophisticated properties.

Note that both the SPR and the GSK vectors may consist of a point-formed value in FIGS. 8a and 8b which need not then contain any information other than direction, i.e. phase angle.

One can go a step further and provide a video display unit with a covering sheet having a window for a relevant quotient field, thus masking off disturbances. Sensors may also be placed over selected portions of the display, and the output signals from these can be used as input signals for simple condition circuits, the output signals of which can be used in many ways, e.g. as blocking or separation signals for the amounts of relevant vectors.

The method of the invention is also characterized in that the lobes are turned, momentarily or continuously, in relation to relevant vectors in the impedance diagram, this being achieved by altering the setting to a phase-generating part of the device, e.g. so that $\phi$ in FIG. 5a is varied.

Swedish patent application No. 351,493 (1971) describes a device for increasing phase-selectivity via frequency duplication. The device described differs essentially from the present invention, but has the same basic idea of improving the conventional synchronous detector with the aid of supplementary circuits and functions.

The invention can be varied in many ways within the scope of the following claims.

What is claimed is:

1. A device for monitoring whether a test object includes a detectable physical characteristic of a particular type in the presence of other physical characteristics of a different type, comprising:
   at least one phase-sensitive detector responsive to at least one phase sensitive input signal for generating at least one phase sensitive output signal in the presence of said other detectable physical characteristics;
   and at least one signal-operating means responsive to said at least one phase sensitive output signal for detecting said detectable physical characteristic and including means for multiplying and/or dividing said at least one sensitive output signal with a reference signal to enhance the detection of said detectable physical characteristic by a vector transformation of said at least one phase sensitive output signal to increase the number of sensitivity lobes for the device to more than two by said multiplying and/or dividing means in multiplying or dividing said phase sensitive output signal and said reference signal, and wherein said at least one signal-operating means includes means for rotating the lobes in relation to the input signals by changing the phase angle of the incoming signal, and said means for rotating further includes means for rotating the lobes in relation to the signal induced by the different type quantity so that this falls between two adjacent lobes where the sensitivity is lower than for the signal induced by the quantity of said particular type.

2. A device for monitoring whether a test object includes a detectable physical characteristic of a particular type in the presence of other physical characteristics of a different type, comprising:

at least one phase-sensitive detector responsive to at least one phase sensitive input signal for generating at least one phase sensitive output signal in the presence of said other detectable physical characteristics;

and at least one signal-operating means responsive to said at least one phase sensitive output signal for detecting said detectable physical characteristic, and including means for multiplying and/or dividing said at least one sensitive output signal with a reference signal to enhance the detection of said detectable physical characteristic by a vector transformation of said at least one phase sensitive output signal, and including means for forming a quotient $A^2/2 \sin 2\alpha$ and means to generate a signal equal to the magnitude $|A|$ and to include this as the denominator in subsequent vector transformation.

3. A device as claimed in claim 2, in which said signal-operating means further includes means for multiplying to form at least two products by two serially connected multipliers.

4. A device for monitoring whether a test object includes a detectable physical characteristic of a particular type in the presence of other physical characteristics of a different type, comprising:

at least one phase-sensitive detector responsive to at least one phase sensitive input signal for generating at least one phase sensitive output signal in the presence of said other detectable physical characteristics;

and at least one signal-operating means responsive to said at least one phase sensitive output signal for detecting said detectable physical characteristic and including means for multiplying and/or dividing said at least one sensitive output signal with a reference signal to enhance the detection of said detectable physical characteristic by a vector transformation of said at least one phase sensitive output signal, and wherein the control signals of at least two phase-sensitive detectors are substantially displaced by different phase angles in relation to each other by $N \times 45$ degrees, where N represents an integer, and said at least one signal-operating means includes means for forming a quotient $A^2/2 \sin 2\alpha$ and means to generate a signal equal to the magnitude $|A|$ and to include this as the denominator in subsequent vector transformation.

5. A device for monitoring whether a test object includes a detectable physical characteristic of a particular type in the presence of other physical characteristics of a different type, comprising:

at least one phase-sensitive detector responsive to at least one phase sensitive input signal for generating at least one phase sensitive output signal in the presence of said other detectable physical characteristics;

and at least one signal-operating means responsive to said at least one phase sensitive output signal for detecting said detectable physical characteristic and including means for multiplying and/or dividing said at least one sensitive output signal with a reference signal to enhance the detection of said detectable physical characteristic by a vector transformation of said at least one phase sensitive output signal, and said signal-operating means further includes means for multiplying to form at least two products by two serially connected multipliers.

6. A device for monitoring whether a test object includes a detectable physical characteristic of a particular type in the presence of other physical characteristics of a different type, comprising:

at least one phase-sensitive detector responsive to at least one phase sensitive input signal for generating at least one phase sensitive output signal in the presence of said other detectable physical characteristics;

and at least one signal-operating means responsive to said at least one phase sensitive output signal for detecting said detectable physical characteristic and including means for multiplying and/or dividing said at least one sensitive output signal with a reference signal to enhance the detection of said detectable physical characteristic by a vector transformation of said at least one phase sensitive output signal, and wherein the control signals of at least two phase-sensitive detectors are substantially displaced by different phase angles in relation to each other by $N \times 45$ degrees, where N represents an integer, and said at least one signal-operating means further includes means for multiplying to form at least two products by two serially connected multipliers.

7. A device for monitoring whether a test object includes a detectable physical characteristic of a particular type in the presence of other physical characteristics of a different type, comprising:

at least one phase-sensitive detector responsive to at least one phase sensitive input signal for generating at least one phase sensitive output signal in the presence of said other detectable physical characteristics;

and at least one signal-operating means responsive to said at least one phase sensitive output signal for detecting said detectable physical characteristic and including means for multiplying and/or dividing said at least one sensitive output signal with a reference signal to enhance the detection of said detectable physical characteristic by a vector transformation of said at least one phase sensitive output signal, said signal-operating means generates a control signal fed to at least one of said at least one detector and which further includes means for varying as a function of the phase alteration of signals which are at least partially derived from the test object.

* * * * *